United States Patent
Weiss

(10) Patent No.: US 6,488,622 B1
(45) Date of Patent: Dec. 3, 2002

(54) METHOD AND AID FOR THE EARLY RECOGNITION OF SUNBURN

(76) Inventor: Marcus Weiss, Moltkestrasse 22, D-67655 Kaiserslautern (DE)

( * ) Notice: Subject to any disclaimer, the term of this patent is extended or adjusted under 35 U.S.C. 154(b) by 0 days.

(21) Appl. No.: 09/762,758
(22) PCT Filed: Aug. 5, 1999
(86) PCT No.: PCT/EP99/05665
§ 371 (c)(1), (2), (4) Date: Feb. 9, 2001
(87) PCT Pub. No.: WO00/09011
PCT Pub. Date: Feb. 24, 2000

(30) Foreign Application Priority Data

Aug. 12, 1998 (DE) .......................... 198 36 464

(51) Int. Cl.⁷ ................................ A61B 5/00
(52) U.S. Cl. ...................... 600/306; 600/556
(58) Field of Search ................. 600/306, 556, 600/310; 250/338.1, 372, 365

(56) References Cited

U.S. PATENT DOCUMENTS

| 3,967,124 | A | * | 6/1976 | Strutz ........................ 250/365 |
| 4,423,736 | A | | 1/1984 | De Witt et al. |
| 4,882,598 | A | * | 11/1989 | Wulf ....................... 250/338.1 |
| 5,241,468 | A | | 8/1993 | Kenet |
| 5,760,407 | A | * | 6/1998 | Margosiak et al. ....... 250/461.1 |

FOREIGN PATENT DOCUMENTS

WO    WO 93 16635    9/1993

* cited by examiner

Primary Examiner—Kevin Shaver
Assistant Examiner—Navin Natnithithadha
(74) Attorney, Agent, or Firm—McGlew and Tuttle, P.C.

(57) ABSTRACT

A method for the early detection of sunburn is provided in which the reflection spectrum of the irradiated skin is considered. A color change made perceptible to the human eye is obtained from the specific absorption and reflection behavior. The change is made to occur when a predetermined borderline spectrum is reached. A device is also provided that changes the reflection spectrum of the irradiated skin, which is determined by the specific absorption and reflection behavior, such that the changed reflection spectrum brings about a color change perceptible to the eye when a predetermined borderline spectrum is reached, whereas no color change perceptible to the eye is yet noticeable if the reflection spectrum is unchanged. The device is used with the method including: defining a borderline spectrum by irradiating a skin area of a person with a predetermined radiation dose and measuring the reflection spectrum of the irradiated skin area after the end of the irradiation; defining a target spectrum that is perceived by the eye in a shade deviating from the natural skin color; and determining a transmission, reflection or emission spectrum by forming the quotient from the individual values of the target spectrum divided by the corresponding individual values of the borderline spectrum.

20 Claims, 4 Drawing Sheets

METHOD AND AID FOR THE EARLY RECOGNITION OF SUNBURN

FIELD OF THE INVENTION

The present invention pertains to a method for the early detection of sunburn, to an auxiliary means for the early detection of sunburn, as well as to a method for determining a suitable transmission, reflection or emission spectrum of an auxiliary means.

BACKGROUND OF THE INVENTION

Interest has been increasingly focused in the past years on research into the effects of UV rays on humans. An excessively intense irradiation of the skin with UV light leads, among other things, to sunburn in humans. Signs of sunburn also include tenderness and functional impairment, besides reddening, swelling and overheating of the irradiated skin area. These reactions are signs of an inflammation, as a consequence of which damage to the epidermal cells may develop. Mediators, including prostaglandins, which lead to a dilatation of the blood vessels and to painful burning in the case of sunburn, are released in the process. The immigration and cytolysis of numerous cells occur during the further course. Besides these temporary consequences of a sunburn, permanent skin damage may also occur, depending on the intensity of the irradiation and the sensitivity of the particular person, e.g., due to a change in the genetic information in the cell nucleus, which may cause skin cancer in the worst case.

Since the ozone layer filters UVB and UVC components out of the natural solar radiation, increasing amounts of this radiation reach the surface of the earth as the ozone layer is increasingly destroyed. In addition, man is increasingly frequently exposed to natural UV radiation in the form of sunlight or natural UV radiation in solaria in order to meet the ideal of beauty of a tanned body. An increase in the number of cases of skin cancer was able to be observed in the wake of these developments.

It has now been ascertained that there is a direct relationship between the radiation dose to which a person is exposed and the probability of developing skin cancer.

To prevent skin damage as a consequence of sunburn, a certain UV radiation dose must not be exceeded within a certain time interval. The radiation dose that is currently still considered to be medically acceptable is the radiation dose that leads to a visible red coloration after 24 hours and is called the minimal erythema dose (MED). The value of this dose depends on the skin type and the pretanning of the person.

The fundamental problem in avoiding sunburn is the time delay with which the signs of sunburn appear after irradiation. Since the inflammation reaches its maximum only about 24 hours after the irradiation, it is not sufficient to avoid sunlight after the first reddening of the skin is observed in order to avoid a sunburn because the medically harmless radiation dose had already been exceeded by that time. A further irradiation going beyond the harmless MED radiation should rather be avoided already at the time at which an incipient sunburn is not yet perceptible.

To determine this point in time, a method and a device, with which it can be determined how long a person can still continue to be exposed to UV irradiation without damage have been known from WO 93/16635 and U.S. Pat. No. 4,882,598. A skin area is irradiated and its reflection is subsequently measured here. Based on these values, a reflection coefficient can be determined, which can be assigned to a certain degree of reddening of the skin. The drawback of this procedure is the complicated measuring means and evaluation of the measurement results, so that the method and the device are unsuitable for the common use, e.g., during tanning.

In addition, it has been known from U.S. Pat. No. 4,432,736 that the intensity of the reddening of the skin and thus the intensity of the sunburn can be inferred from the specific reflection spectrum of irradiated skin areas. The method disclosed there is, however, limited to an exact determination of the remission spectrum with subsequent evaluation of the reflection curve. The fact that a complicated apparatus, by means of which the remission spectrum is first determined and subsequently evaluated, is needed to detect the remission spectrum is a drawback in this case as well. Thus, a complicated apparatus and a time-consuming procedure are consequently needed to obtain information on the degree of sunburn, and this approach is therefore rather impractical.

Furthermore, it has been known from DE 31 37 326 A1 that the degree of tanning of the human skin can be determined by means of a device in which the skin is exposed to a light source of a defined spectral composition and the light is again received by a light sensor. This arrangement is tailored to and at the same time limited to the determination of the degree of tanning of the human skin. The tanning of human skin depends on the melanin content in the skin and begins only after a sunburn. Thus, it is not possible to predict a sunburn to be expected.

Finally, it has been known from DE 34 19 872 A1 that the coloring of the skin as a consequence of solar radiation can be determined by means of logically ordered color carriers. Even though the instantaneous state of the color of the skin can thus be determined, a sunburn is noticed in the manner disclosed in DE 34 19 872 A1 only after it has occurred because the red coloration as a consequence of sunburn follows the irradiation with a time delay only and reaches its maximum approx. 24 hours after the irradiation. Thus, this device is not suitable for avoiding sunburn.

SUMMARY AND OBJECTS OF THE INVENTION

Against this background, the basic object of the present invention is to provide a reliable, easy-to-handle and effective method for the early detection of a sunburn as well as a corresponding auxiliary means therefor.

The present invention is based on the discovery that the UV irradiation of the skin leads to skin changes, e.g., the accumulation of hemoglobin and oxyhemoglobin in the near-surface layers of the skin. Based on the characteristic absorption behavior of these substances, the reflection spectrum of the skin is changed to the extent that a sunburn is perceived as reddening of the skin beginning from a certain degree of change. A certain reflection spectrum can be graphically assigned to each grade of reddening of the skin, and any change in the shade thus brings about a changed reflection spectrum.

In addition, it has been recognized that the change in the reflection spectrum and thus the intensity of the reddening or the extent of the sunburn will still increase even when there is no further irradiation. The maximum of this development is reached after about 24 hours. It is also assumed in the present invention that the change in the red coloration of the skin over time as a function of the UV radiation dose is known and is essentially the same within certain limits.

As was already mentioned, a medically harmless radiation dose, which just does not yet lead to any skin damage, can be assigned for each person depending on his or her skin type. This dose can be determined experimentally and leads to a just visible red coloration of the skin after about 24 hours, after the sunburn shows its maximum effects. Typical reflection spectra, which describe the characteristic course of the reddening of the skin in the case of a sunburn, can be assigned to this radiation dose, also called MED, as a function of time. Of this large number of reflection spectra, precisely the spectrum at the time of the end of the irradiation is significant for the present invention, because this spectrum indicates unambiguously when a person must stop being exposed to further radiation if the delayed skin reaction should not lead to any more damage.

The insufficient color sensitivity of the human eye is a problem in utilizing this discovery. A shade is determined basically by the mixing ratio with which individual spectral ranges come together. If all spectral ranges are changed uniformly, this does not affect the mixing ratio, i.e., the shade remains the same, and only the lightness is changed. If, by contrast, only individual spectral ranges are changed, this leads to a change in the mixing ratio, which can lead to a change in the shade. However, the human eye can perceive a significant change in shade only when the change exceeds a certain threshold value.

The addition of different spectral components of the non-irradiated skin leads to the perception of a shade typical of the skin in the human eye. Due to the increasing concentration of hemoglobin and oxyhemoglobin as a consequence of UV irradiation, there is increased absorption of spectral components in the wavelength ranges from 400 to approx. 630 nm. This leads to reduced reflection of the light in these wavelength ranges, so that the shade perceptible to the human eye is composed of another mixing ratio of the different spectral ranges. However, this leads to a perceptible red coloration of the skin, which becomes increasingly intense with increasing concentration, only beginning from a certain threshold concentration of hemoglobin and oxyhemoglobin. Even though the reflection spectrum of the skin is changed below the threshold concentration, the change is not perceptible to the human eye as a color change to red. The reflection spectrum that indicates that the MED radiation has been reached and thus shows that more radiation should be avoided also falls within this range, which is still imperceptible to the naked eye. This spectrum will hereinafter be called the borderline spectrum.

Thus, the person is unable to detect this slight change in the shade of the skin until the just still tolerable radiation dose is reached without suitable auxiliary means.

The present invention makes this borderline spectrum visible, which does not yet lead to a color change of the skin when viewed with the naked eye in daylight, directly to the eye. This is achieved by selectively changing the borderline spectrum over at least part of the entire spectral range, where wavelength ranges from 620 nm to 700 nm possibly remain unchanged, whereas the other wavelength ranges from 400 to 620 nm are absorbed to an increased extent.

If the spectrum of the auxiliary means according to the present invention is correspondingly adapted, a clearly perceptible color change can be achieved when a certain reflection spectrum of the skin is reached when viewing the skin with a light to be specified (sunlight or artificial light).

The advantage of the present invention is that a simple and yet reliable method and auxiliary means have been created for the early detection of sunburn, which method can be carried out without a complicated device. The method can be correspondingly carried out and the device can be manufactured at an extremely low cost and they are thus accessible to many users.

The user obtains the result of the examination immediately and without complicated evaluation by means of reference curves, reference areas or charts. Possible sources of error are thus avoided and the reliability of the present invention is at the same time increased.

The examination of the skin is not linked with any discomfort because it is carried out in a completely contactless manner. Free movement is possible during the examination and the result is obtained immediately. Even an examination performed from a distance yields reliable results. This is advantageous especially in the case of supervising children, in whom a sunburn causes damage sooner than adults and who should therefore be checked for signs of a sunburn especially frequently.

Another advantage of the present invention is its independence from the skin type and the skin color. What is decisive for the method according to the present invention is the appearance of a certain reflection spectrum, which is made visible by a color change. This reflection spectrum is caused by a certain radiation dose, which may be different for different skin types and skin colors, but it always leads to sunburn when it is reached. This means that even though people with different skin types or skin colors can expose themselves to an equal UV radiation over different lengths of time, they should stop being exposed when a red coloration visible with the auxiliary means has been reached in order to avoid skin damage.

A preferred embodiment of the present invention is a filter with a corresponding transmission spectrum, because a filter can be manufactured and handled in an extremely simple manner. In addition, there are situations in which an auxiliary means meaningfully comprises a reflecting surface with a corresponding remission spectrum, e.g., a mirror. Such a case would occur, e.g., when one would like to detect a beginning sunburn in the face himself. Daylight is a suitable light source for the irradiation, but the auxiliary means may also be designed for viewing in artificial light.

Technically more complicated but just as reliable in operation is the use of a light source with a corresponding emission spectrum. A light source according to the present invention has increased emission in the red range compared with the other spectral ranges.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
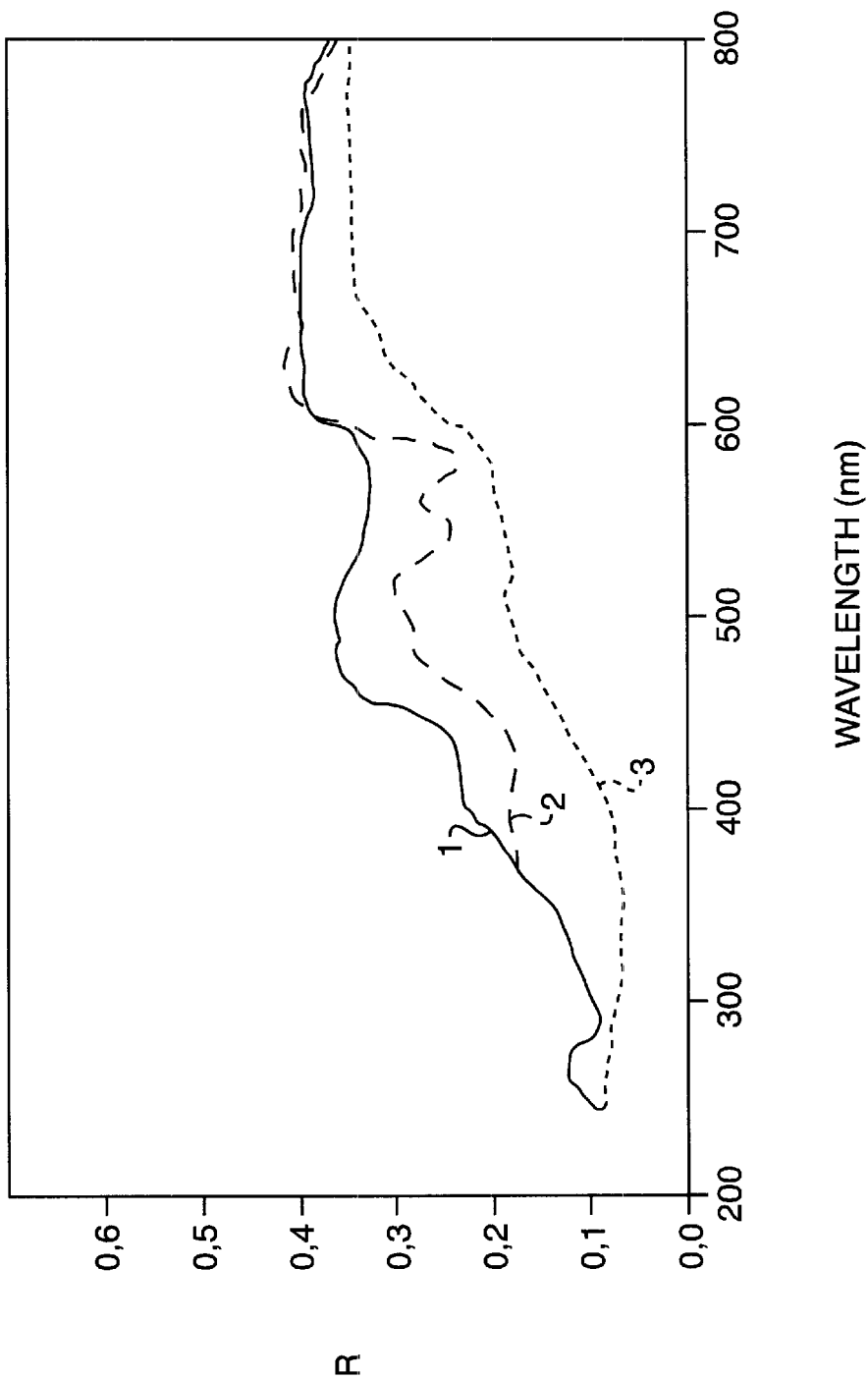
FIG. 1 is a diagram showing remission spectroscopic measurements on human skin before and after UV irradiation.

Referring to the drawings in particular, FIG. 1 shows three different curves of remission spectroscopic measurements on human skin, which curves are designated by the numbers 1 through 3. Curve 1 shows the reflection spectrum of non-irradiated skin. The degree of reflection in the wavelength ranges between 250 nm and 300 nm varies around 0.1.

Then, between 300 nm and 400 nm, it increases linearly to 0.23. There is only a slight increase in the degree of reflection from 400 nm to 440 nm before a steep increase to approx. 0.37 can be seen between 440 nm and 460 nm. The degree of reflection gradually decreases to 0.33 between 500 nm and 600 nm before it increases to a value of 0.4 at approx. 600 nm to remain constant up to approx. 800 nm.

The spectrum visible to the human eye begins at 420 nm, which is perceived by the eye as a blue shade and reaches 700 nm, which corresponds to the red shades, over green and yellow shades. The skin color perceived by the human eye is obtained from the different spectral components of the irradiation source, which are reflected at different intensities by the skin according to curve 1 and are then perceived by the person due to their addition in a certain shade.

Curve 2 shows a remission spectrum of the human skin after UV irradiation, which has led to a sunburn with pronounced red coloration. While the degree of reflection undergoes hardly any change in the range between 600 nm and 700 nm, the radiation is reflected markedly less intensely in the rest of the visible wavelength range. The minima at 540 nm and 570 nm as well as the maximum between them are especially significant. The red coloration perceived by the eye is obtained from the unchanged high reflection of the red component of the spectrum and the simultaneously intense absorption of the other spectral ranges.

Finally, curve 3 shows the reflection spectrum of suntanned skin without sunburn. The red component is not so dominant here compared with the other color components as in curve 2, so that the addition of the spectral ranges finally leads to a brown shade.

Figure 2:
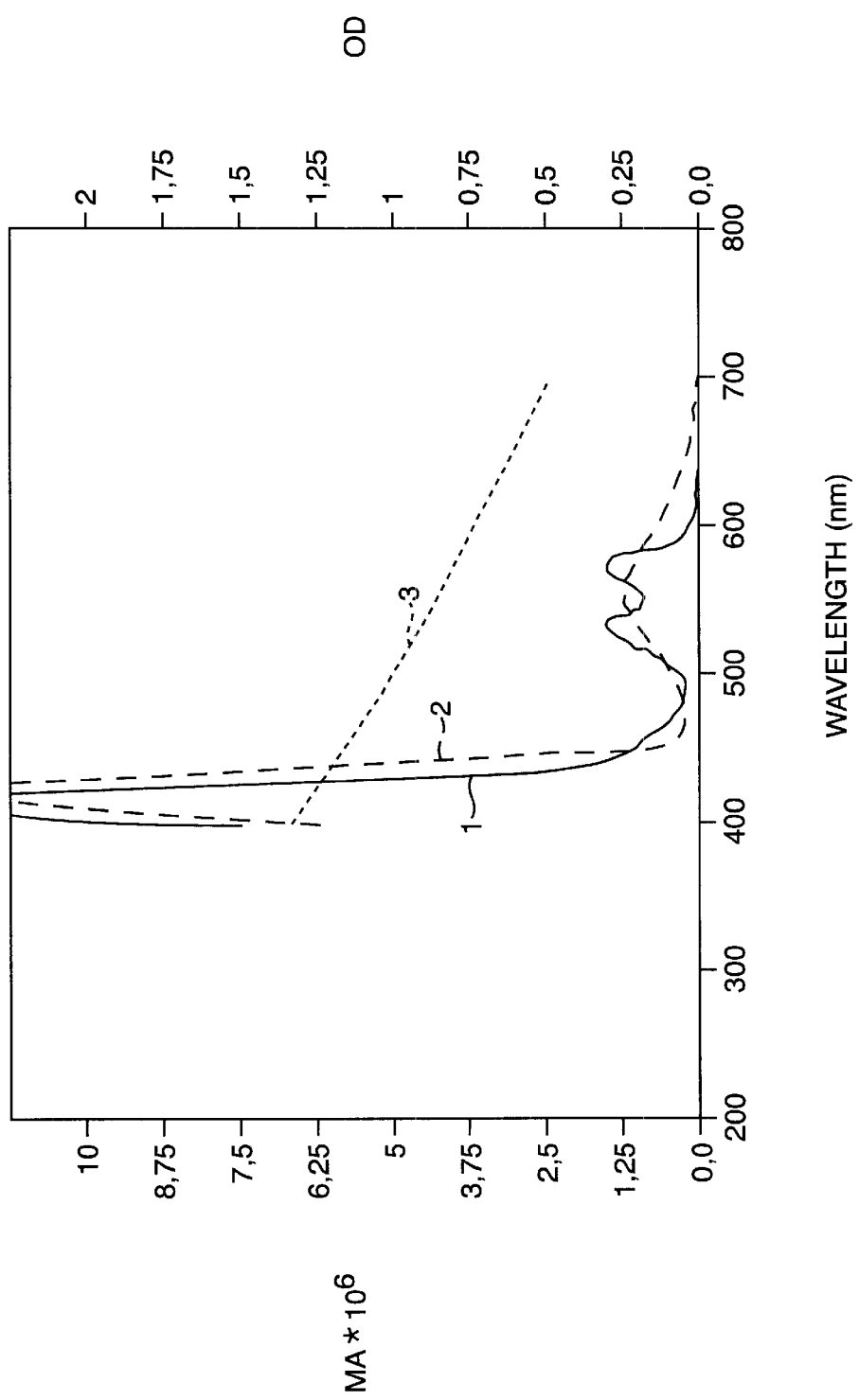
FIG. 2 is a diagram showing the changes in the molar absorption coefficient of oxyhemoglobin and hemoglobin as well as in the optical density of melanin.

FIG. 2 shows the molar absorption coefficients (MAs) of oxyhemoglobin in curve 1 and of hemoglobin in curve 2 as well as the optical density (OD) of melanin in curve 3 as a function of the wavelength of the light. The molar density (OD) is dimensionless. The molar absorption coefficient (MA) has the dimension $MA = E \cdot 10^{-6}$ [1/mole m].

The high absorbing capacity of oxyhemoglobin and hemoglobin in the range of 400 nm to 450 nm is remarkable, while there is practically no absorption in the wavelength ranges of 600 nm and higher, i.e., in the range of the red shades. In addition, the maxima in the range of 540 nm to 570 nm with the minimum located between them are characteristic in curve 1. These are responsible for the reduction in the degree of reflection in the range of these wavelengths, as was described under FIG. 1.

Figure 3:
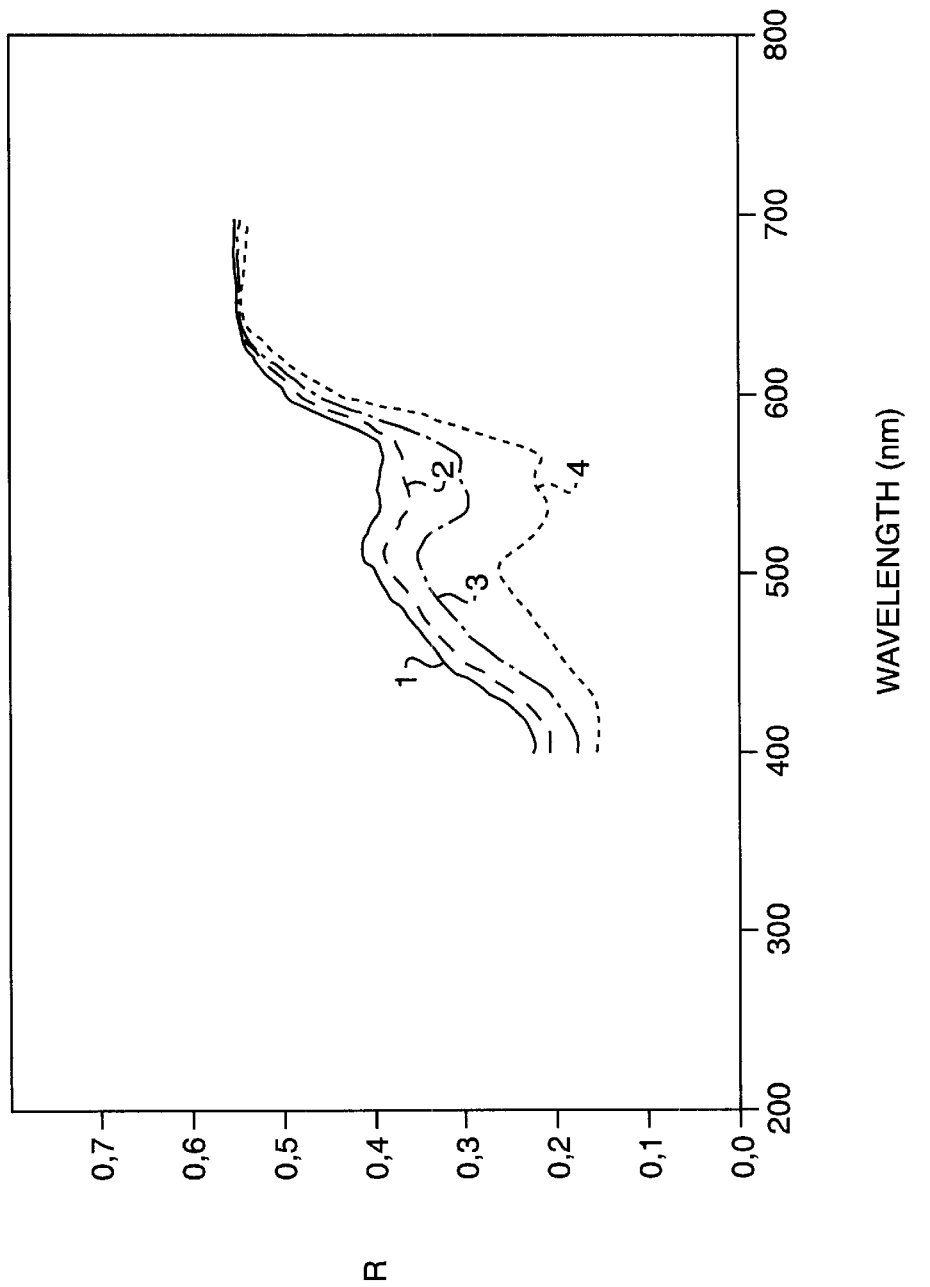
FIG. 3 is a diagram showing remission spectroscopic measurements on human skin at different points in time after UV irradiation.

In FIG. 3, curves 1 through 4 show remission spectroscopic measurements on human skin following UV irradiation at different points in time in the course of a sunburn. Curve 1 shows the reflection spectrum of human skin before irradiation and corresponds essentially to curve 1 in FIG. 1. There is a change in the reflection spectrum according to curve 2 already shortly thereafter. The absorption behavior and the reflection behavior of the skin, which is linked therewith, are affected by the beginning accumulation of oxyhemoglobin and hemoglobin in the near-surface skin layers. Compared with the spectral range of approx. 600 nm to 700 nm, the absorption of the other spectral ranges is not yet high enough to make visible a reddening of the skin to the naked eye. The continuous accumulation of oxyhemoglobin later leads to increased absorption in the spectral ranges from 400 nm to 600 nm. Beginning from a certain borderline spectrum, the percentage of reflected red light is so high compared with the other spectral ranges that a color change from the natural skin color to red is perceptible to the human eye. This borderline spectrum is shown in curve 3.

Even though there is no further irradiation, the intensity of the red coloration and of the sunburn continue to increase as a consequence of the delayed reaction of the skin. The red coloration reaches its higher value after about 24 hours to slowly subside thereafter. The remission spectrum recorded after about 24 hours is shown in curve 4. A marked red coloration of the skin is recognizable to the human eye.

Figure 4:
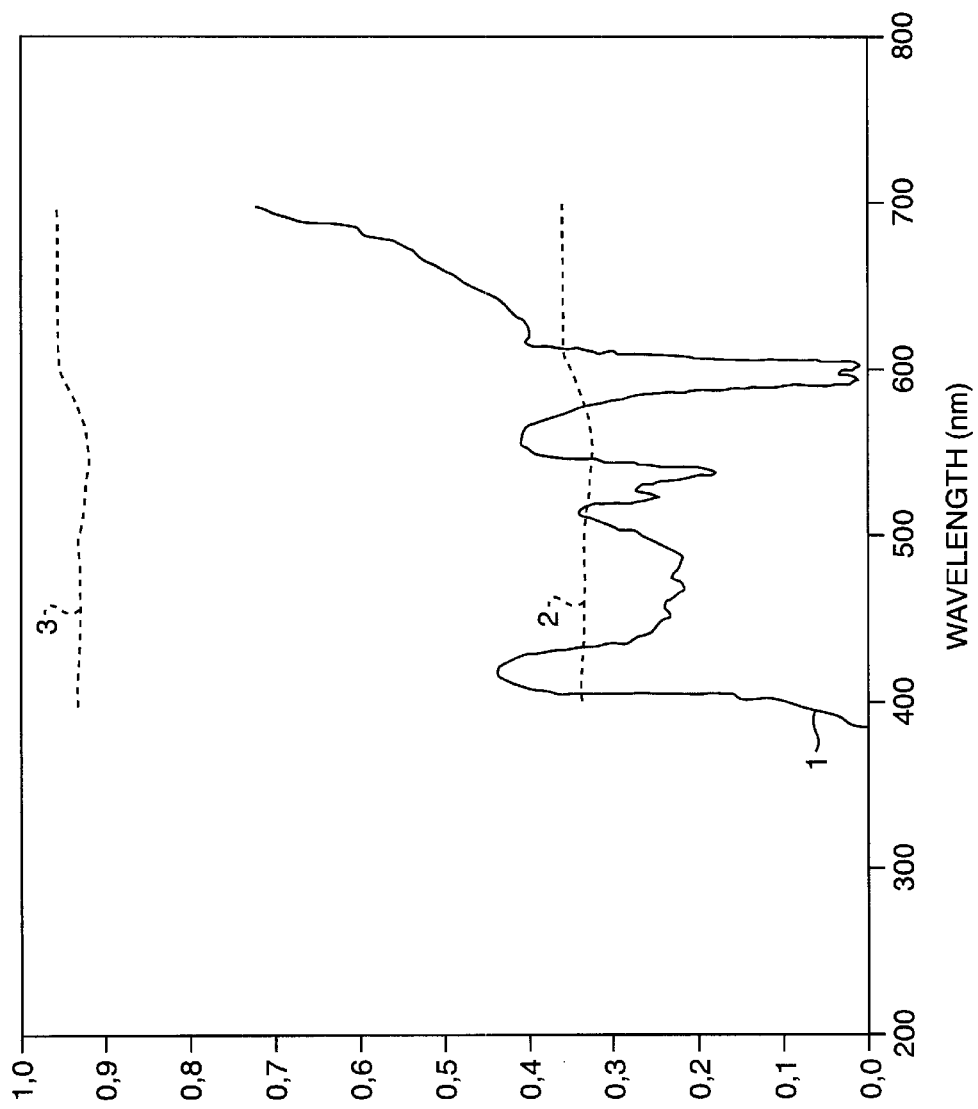
FIG. 4 is a diagram showing three transmission spectra of a filter according to the present invention and reflection spectra of a mirror according to the present invention.

FIG. 4 shows possible transmission spectra of an auxiliary means for the early detection of sunburn in curves 1, 2 and 3. The light reflected from the skin reaches the auxiliary means, e.g., a filter, in the form of a remission spectrum. The reflection spectrum of the skin is changed in a specific manner due to the characteristic transmission spectrum of this light. The spectral ranges with red shades are let through by the filter possibly unhindered, whereas the other spectral ranges are absorbed more intensely. The consequence of this is that the effect that occurs due to the increased absorption of spectral ranges in the range of 400 nm to 600 nm as a consequence of the accumulation of oxyhemoglobin and hemoglobin in the skin is additionally intensified for the human eye. As a result, the human eye can perceive a red coloration of the skin already at a point in time at which no change in the color of the skin would be able to be detected without the auxiliary means.

A transmission spectrum suitable for this purpose is shown in curve 1, which was determined experimentally. It shows the higher degree of transmission in the range of 700 nm, i.e., in the red range, while the degree of transmission is markedly lower in spectral ranges with shorter wavelengths. This filter has a neutral color with respect to sunlight because of the color composition and leads only to a darkening.

By contrast, curves 2 and 3 show transmission spectra determined according to patent claim 18, which are identical in terms of the shape of the curve, and only different lightnesses are obtained on viewing. To determine them, the medically harmless radiation is determined for any person. The MED value is currently used for this value, but it may change if new medical discoveries are made. However, it will hereinafter be called the MED value. The remission spectrum of the irradiated skin area is determined here immediately after the end of the MED irradiation. A method and a device for carrying out such measurements have been known from WO 93/16635 and U.S. Pat. No. 4,432,736. This remission spectrum is the borderline spectrum at which further irradiation must be avoided. Since no color change can be detected by the naked eye during the transition from the reflection spectrum of non-irradiated skin to the borderline spectrum, the transmission (reflection or emission) spectrum of an auxiliary means must change the borderline spectrum to the extent that a color change perceptible to the eye, e.g., to red, will take place when the borderline spectrum is reached.

This happens if the borderline spectrum is changed by the auxiliary means into a target spectrum, e.g., according to curve 3 in FIG. 3. To determine the transmission spectrum necessary for this, a borderline spectrum is divided in this example in each spectral range by the corresponding value of a remission spectrum (e.g., curve 3 in FIG. 3), which is perceived as red by the eye. The changes in the quotient are obtained from a transmission spectrum according to the present invention, which shows the desired color change taking place when the borderline spectrum is reached. A shift of the transmission spectrum in the direction of the ordinate does not cause any change in the ability of this transmission spectrum to display the borderline spectrum by a color change, but it affects only the lightness of the shade of the skin area being viewed through the filter.

Since a large number of spectra, which may also lead to shades other than red, are conceivable as the target spectrum, a transmission spectrum that indicates the reaching of the borderline spectrum by a color change into another color can also be determined in the manner according to the present invention.

It was assumed in the above explanation of the present invention that after a radiation dose at the level of the MED value, the time has come to avoid further irradiation to avoid sunburn. Accordingly, the reflection spectrum corresponding to this radiation is used as a borderline spectrum, which is made visible according to the present invention. It is, of course, also possible to select as the borderline spectrum another reflection spectrum from the large number of reflection spectra which describe the course of sunburn over time. If, e.g., a can be assigned to the selected borderline spectrum.

By selecting certain borderline spectra, it is thus possible to define different filter types which can be assigned to different sunburn warning levels.

Since the reflection spectrum of the skin depends not only the reflection properties of the skin but also on the emission spectrum of the radiation source, different types of filters, whose transmission spectrum is adapted to the emission spectrum of the particular radiation source, are also necessary for the different radiation sources, e.g., sunlight, UV tubes in solaria, etc.

While specific embodiments of the invention have been shown and described in detail to illustrate the application of the principles of the invention, it will be understood that the invention may be embodied otherwise without departing from such principles.

What is claimed is:

1. A method for the early detection of sunburn of an individual, the method comprising the steps of:
    changing an apparent reflection spectrum of irradiated skin of the individual, which arises from a specific absorption and reflection behavior of the individual's skin, by providing a color change perceptible to the human eye when a predetermined borderline spectrum is reached in the reflection spectrum of irradiated skin of a subject.

2. A method in accordance with claim 1, wherein the borderline spectrum corresponds to the reflection spectrum that appears after the end of the irradiation of the skin with the minimum erythema dose value.

3. A method in accordance with claim 1, wherein the degree of reflection of the irradiated skin is reduced by 5% at least in the wavelength range from 400 nm to 620 nm in the sun.

4. A method in accordance with claim 1, wherein the degree of reflection of the irradiated skin is reduced to a minimum at least in the wavelength range from 520 nm to 570 nm.

5. A method in accordance with claim 1, wherein the degree of reflection of the irradiated skin remains essentially unchanged in the wavelength range form 650 nm to 700 nm.

6. A method in accordance with claim 1, wherein a transparent medium with a defined reflection spectrum, e.g., a filter, or a reflecting surface with a defined reflection spectrum, e.g., a mirror, or a light source with a predetermined emission spectrum is used to change the reflection spectrum of the irradiated skin.

7. An auxiliary device for the early detection of sunburn, the device comprising:
    a reflection spectrum changer for changing a reflection spectrum of the irradiated skin, which is determined by a specific absorption and reflection behavior of the irradiated skin, such that the changed reflection spectrum brings about a color change perceptible to the eye when a predetermined borderline spectrum is reached, whereas no color change perceptible to the eye is yet noticeable if the reflection spectrum is unchanged.

8. An auxiliary device in accordance with claim 7, wherein the borderline spectrum corresponds to the reflection spectrum that appears after the end of the irradiation with the minimum erythema dose value.

9. An auxiliary device in accordance with claim 7, wherein the device is suitable for reducing the degree of reflection of the irradiated skin by 5% at least in the wavelength range from 400 nm to 650 nm in the sun.

10. An auxiliary device in accordance with one of the claim 7, wherein the device is suitable for the degree of reflection of the irradiated skin to have a minimum at least in the wavelength range from 500 nm to 600 nm.

11. An auxiliary device in accordance with claim 7, wherein the device leaves the degree of reflection of the irradiated skin essentially unchanged in the wavelength range form 650 nm to 700 nm.

12. An auxiliary device in accordance with claim 7, wherein the reflection spectrum changer includes a transparent medium filter.

13. An auxiliary device in accordance with claim 12, wherein the reflection spectrum changer changes the transmission spectrum, lowering the transmission between the wavelength of 400 nm and 600 nm to an average of about 30% and lowering the transmission between the wavelength of 600 nm and 700 nm to an average of about 55% and also having a minimum transmission at a wavelength between 580 and 610 nm.

14. An auxiliary device in accordance with claim 7, wherein the reflection spectrum changer includes a reflecting surface.

15. An auxiliary device in accordance with claim 14, wherein the reflection spectrum changer lowers the remission between the wavelength of 400 nm and 600 nm to an average of about 30% and lowerers the remission between the wavelength of 600 nm and 700 nm to an average of about 5% and also has a minimum remission at a wavelength between 580 and 610 nm.

16. An auxiliary device in accordance with claim 7, wherein the auxiliary means consists of a light source.

17. An auxiliary device in accordance with claim 7, wherein the device describes the reflection spectrum of the irradiated skin until a borderline spectrum is reached in a skin color-neutral manner.

18. A method for determining a suitable transmission, reflection or emission spectrum of a reflection spectrum changer for changing a reflection spectrum of irradiated skin of an individual, which is based on specific absorption and reflection behavior of the skin of the individual, such tat the changed reflection spectrum brings about at color change perceptible to the eye when a predetermined borderline spectrum is reached, whereas no color change perceptible to the eye is yet noticeable if the reflection spectrum is unchanged, the method comprising the steps of:

defining a borderline spectrum by irradiating a skin area of a person with a predetermined radiation dose and measuring the reflection spectrum of the irradiated skin area after the end of the irradiation;

defining a target spectrum that is perceived by the eye in a shade deviating from the natural skin color; and determining a transmission, reflection or emission spectrum by forming the quotient from the individual values of the target spectrum divided by the corresponding individual values of the borderline spectrum.

19. A method in accordance with claim 18, wherein to define the borderline spectrum, a skin area is irradiated with a radiation dose at the level of the minimum erythema dose value.

20. A method in accordance with claim 18, wherein the target spectrum is defined by the reflection spectrum of the irradiated skin with a red coloration perceptible to the naked eye.

* * * * *